(12) United States Patent
Chin

(10) Patent No.: US 6,951,568 B1
(45) Date of Patent: Oct. 4, 2005

(54) LOW-PROFILE MULTI-FUNCTION VESSEL HARVESTER AND METHOD

(75) Inventor: Albert K. Chin, Palo Alto, CA (US)

(73) Assignee: Origin Medsystems, Inc., Santa Clara, CA (US)

( * ) Notice: Subject to any disclaimer, the term of this patent is extended or adjusted under 35 U.S.C. 154(b) by 320 days.

(21) Appl. No.: 09/614,482

(22) Filed: Jul. 10, 2000

(51) Int. Cl.$^7$ .............................................. A61B 1/00
(52) U.S. Cl. ..................... 606/190; 600/104; 600/121; 600/123
(58) Field of Search ............................... 606/170, 185, 606/190; 600/104, 105, 121, 123, 154

(56) References Cited

U.S. PATENT DOCUMENTS

| | | | | |
|---|---|---|---|---|
| 4,198,959 A | * | 4/1980 | Otani | 600/106 |
| 4,240,411 A | * | 12/1980 | Hosono | 600/154 |
| 4,436,087 A | * | 3/1984 | Ouchi | 600/106 |
| 5,025,778 A | * | 6/1991 | Silverstein et al. | 600/104 |
| 5,503,616 A | * | 4/1996 | Jones | 600/153 |
| 5,569,292 A | * | 10/1996 | Scwemberger et al. | 606/185 |
| 5,722,934 A | * | 3/1998 | Knight et al. | 600/201 |
| 5,817,013 A | * | 10/1998 | Ginn et al. | 600/114 |
| 5,911,694 A | * | 6/1999 | Ikeda et al. | 600/587 |
| 5,916,233 A | * | 6/1999 | Chin | 606/190 |
| 5,938,586 A | * | 8/1999 | Wilk et al. | 600/123 |
| 5,938,680 A | * | 8/1999 | Ginn | 606/190 |
| 5,968,066 A | * | 10/1999 | Fogarty et al. | 606/190 |
| 6,019,720 A | * | 2/2000 | Bito | 600/123 |
| 6,086,583 A | * | 7/2000 | Ouchi | 606/41 |

* cited by examiner

Primary Examiner—Michael H. Thaler
(74) Attorney, Agent, or Firm—Fenwick & West LLP

(57) ABSTRACT

A cannula comprises a main body for accommodating both an endoscopic lumen and a working lumen. The main body of the cannula ends at a point proximal to the distal end of the cannula. Extending distally from the point at which the main body end is an endoscopic dissection shaft of decreased diameter, which houses the endoscopic lumen, but not the working lumen. A transparent tapered tip is positioned on the distal end of the endoscopic dissection shaft. Due to the decreased diameter of the endoscopic dissection shaft, the transparent tapered tip has a small diameter, The main body of the cannula ends in a smoothly contoured face that provides minimal trauma to vessel and other tissue that comes in contact with the face as the cannula is advanced through the surgical site. The endoscope is sealed in the endoscopic lumen by the transparent tapered tip to prevent smudging of the endoscope by surrounding blood or tissue during dissection and during surgical procedures performed by surgical tools housed in an auxiliary lumen. A flexible hood extends from the distal end of the working lumen to the proximal edge of the transparent tapered tip to form a tapered profile to facilitate low dissection force and improved maneuverability, and the flexible hood also prevents blood or tissue from entering into the working lumen.

10 Claims, 7 Drawing Sheets

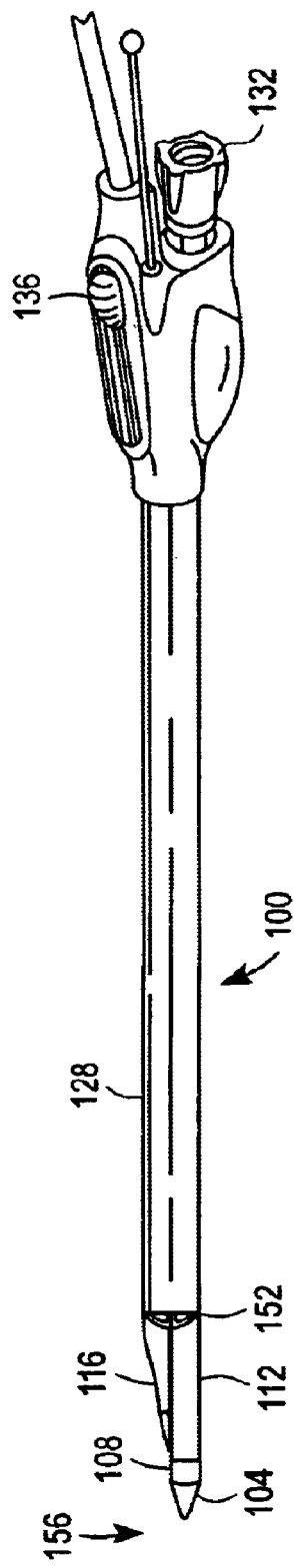
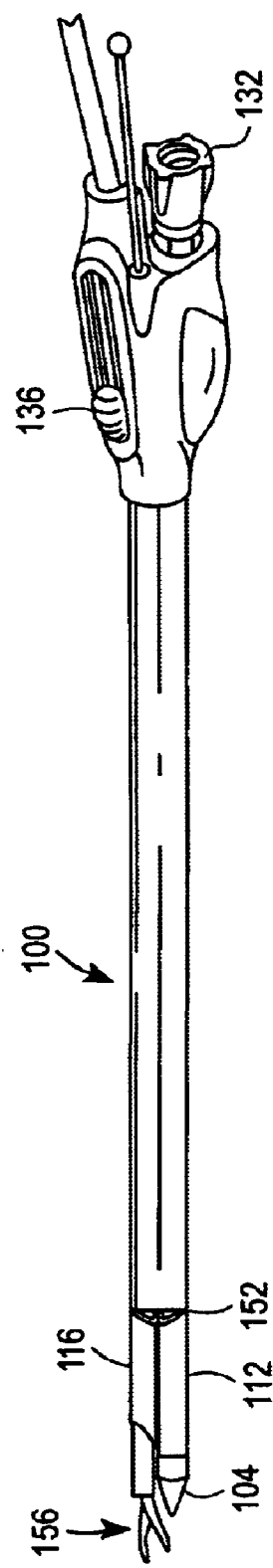
FIG. 2A
FIG. 2B

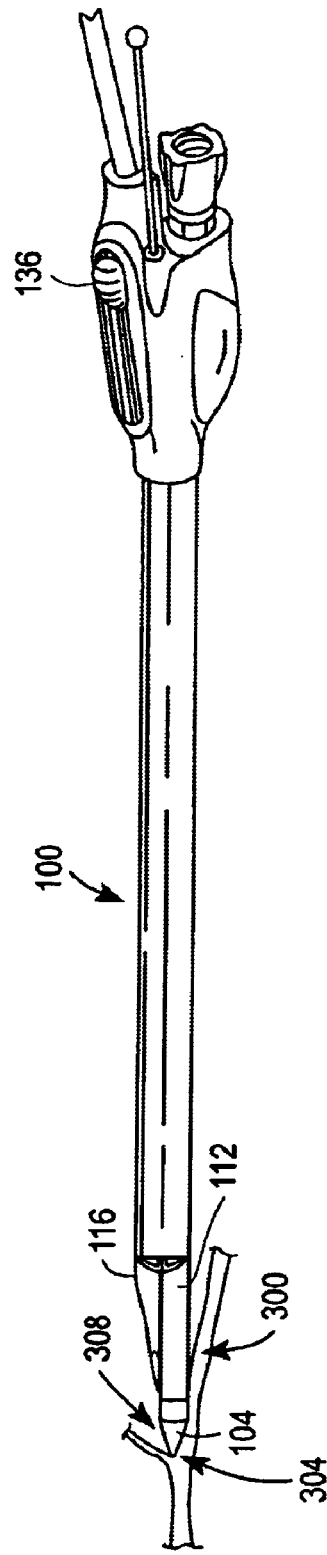
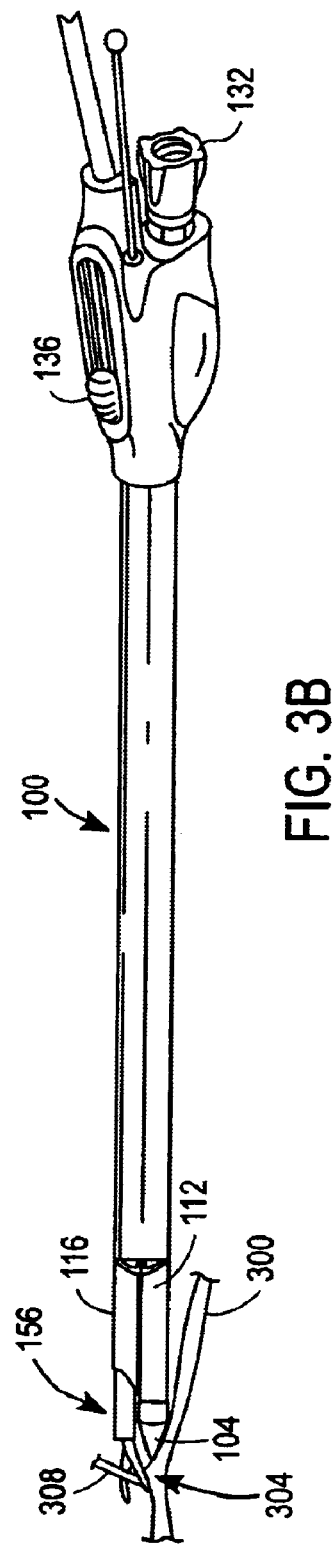
FIG. 3A
FIG. 3B

LOW-PROFILE MULTI-FUNCTION VESSEL HARVESTER AND METHOD

FIELD OF THE INVENTION

The present invention relates to the field of surgical apparatus, and more particularly to endoscopic vessel harvesting.

BACKGROUND OF THE INVENTION

Presently, endoscopic vessel harvesting is conducted in multiple steps. In one procedure, a surgeon inserts a cannula having a lumen housing an endoscope and a transparent tapered tip encasing the distal end of the cannula into an incision. The surgeon advances the cannula under endoscopic visualization through the transparent tip along the sides of a vessel to be harvested to dissect the vessel away from surrounding connective tissue. Then, in order to perform any other surgical procedure, the cannula must be withdrawn from the incision to detach the transparent tapered tip from the cannula to provide an open distal end. The open distal end permits endoscopic shears or other surgical tool to be extended out of the cannula and into the surgical site to perform a surgical procedure, such as cauterization and transection of vessel side branches in a saphenous vein harvesting procedure. As the transection is performed under endoscopic visualization, the cannula must be sufficiently large to accommodate both the endoscope and endoscopic shears. Thus, a cannula having a lumen that can accommodate an endoscope (typically 5 mm) and having at least one other lumen of sufficient diameter to accommodate a surgical tool such as endoscopic shears (typically 5 mm) must have a shaft that is typically 12 mm in diameter. Accordingly, a vessel harvesting cannula with a smaller distal profile is desired to improve maneuverability and to decrease dissection force required to advance the cannula through connective tissues.

SUMMARY OF THE INVENTION

In accordance with the present invention, a cannula comprises a main body for accommodating both an endoscopic lumen and a working lumen. However, in accordance with the present invention, the main body of the cannula ends at a point proximal to the distal end of the cannula. An endoscopic dissection shaft of decreased diameter extends distally from the point at which the main body ends, and the endoscopic dissection shaft houses the endoscopic lumen but not the working lumen. A transparent tapered tip is positioned on the distal end of the endoscopic dissection shaft. Due to the decreased diameter of the endoscopic dissection shaft, the transparent tapered tip is smaller than the tips used in conventional devices. Moreover, the diameter of the endoscopic dissection shaft is also less than the diameter of conventional cannulas. Therefore, the dissection force required to be exerted by the cannula of the present invention is much less than the force required to be exerted by conventional devices to accomplish blunt tissue dissection, and the maneuverability of the cannula of the present invention is also much greater than the maneuverability of conventional devices. However, the larger diameter of the main body of the cannula provides substantially the same tissue dilation as is provided by conventional cannulas. Further, the use of an open working lumen along with the closed tip endoscopic dissection shaft allows the surgeon to perform a surgical procedure under endoscopic visualization at the same time a tip is used for dissection. Additionally, the closed tip enables the endoscope to be kept free of blood and tissue during a surgical procedure.

In one embodiment, the main body of the cannula ends in a smoothly contoured face that provides minimal trauma to vessels and other tissue that comes in contact with the face as the cannula is advanced through the surgical site. In another embodiment, the endoscope is sealed in the endoscopic lumen formed by the small endoscopic dissection shaft, thus preventing smudging of the endoscope by surrounding blood or tissue during surgical procedures. In still another embodiment, a flexible hood extends from the distal end of a working lumen to the proximal edge of the transparent tapered tip. The flexible hood gives the cannula a tapered profile to provide low dissection force and improved maneuverability, and the flexible hood also prevents blood or tissue from entering into the working lumen.

In another embodiment, a pair of endoscopic scissors, a bisector, or shears resides in the working lumen. The scissors are retracted into the working lumen and are extended axially out of the flexible hood via a sliding mechanism including an actuation button on the handle, or by moving the handles of the scissors forward with respect to the cannula. The shaft of the scissors may be keyed to the lumen to maintain the tips of the scissors at a predetermined rotational orientation with respect to the transparent tapered tip, preferably curved inward toward the tip of the device. This allows endoscopic visualization of the entire length of the scissor blades as a side branch is transected, thus ensuring a safe cutting process. The flexible hood also covers the scissor blades as the scissors are advanced out of the working lumen to prevent the scissors from catching vessel branches or connective tissue through which the cannula is advanced.

In another embodiment, a third, smaller diameter lumen extends along the length of the main body of the cannula. The third lumen houses the shaft of a dissection loop that may be used for vessel retraction and dissection of connective tissue from the vessel. The open loop may be pulled back into a matching groove in the contoured face of the main body of the cannula. Docking of the dissection loop in this manner preserves the smooth contour of the device, to minimize friction upon cannula advancement. In an alternate embodiment, a cradled retractor is positioned in the working lumen to ensure that all side branches have been severed during the procedure.

During a surgical procedure, a vessel is isolated via an incision, and the small transparent tapered tip is placed on the adventitial surface of the vessel and advanced along the vessel a sufficient length to allow insertion of a gas-sealing sliding port. The port seals the incision and gas insufflation is initiated. The elongated body of the cannula is advanced through the port with the transparent tip disposed to pass along the length of the vessel along its anterior and posterior aspects, and on either side of each tributary. Minimal dissection force is required to advance the tip through connective tissue due to the low distal profile of the cannula. Then, scissors are extended forward through the cannula to cauterize and cut the tributaries of the vessel being harvested. The center of the tapered tip is placed against the main trunk of the vessel, and the cannula is rotated to place the scissors blades in position to cut the tributaries. Following transection of all tributaries emanating from the vessel, the dissection loop may be used to pass along the length of the vessel in contact therewith to ensure that all attachments have been severed. Thus, the cannula need not be removed from the surgical site to perform surgical procedures within the insufflated anatomical space formed adjacent the vessel being harvested. Moreover, the endoscopic lens is kept free of blood and tissue during the performance of the surgical procedures by the transparent tip that is disposed over the distal end of the lumen containing the endoscope.

BRIEF DESCRIPTION OF THE DRAWINGS

FIG. 1b is a cut-away view of the endoscopic cannula of FIG. 1a.

FIG. 2a is a perspective view of an endoscopic cannula in accordance with the present invention in which endoscopic scissors are retracted.

FIG. 2b is a perspective view of an endoscopic cannula in accordance with the present invention in which endoscopic scissors are extended.

FIGS. 3a and 3b are perspective views of the endoscopic cannula of the present invention, respectively, dissecting and transecting tissue.

DETAILED DESCRIPTION OF THE PREFERRED EMBODIMENTS

Figure 1A:
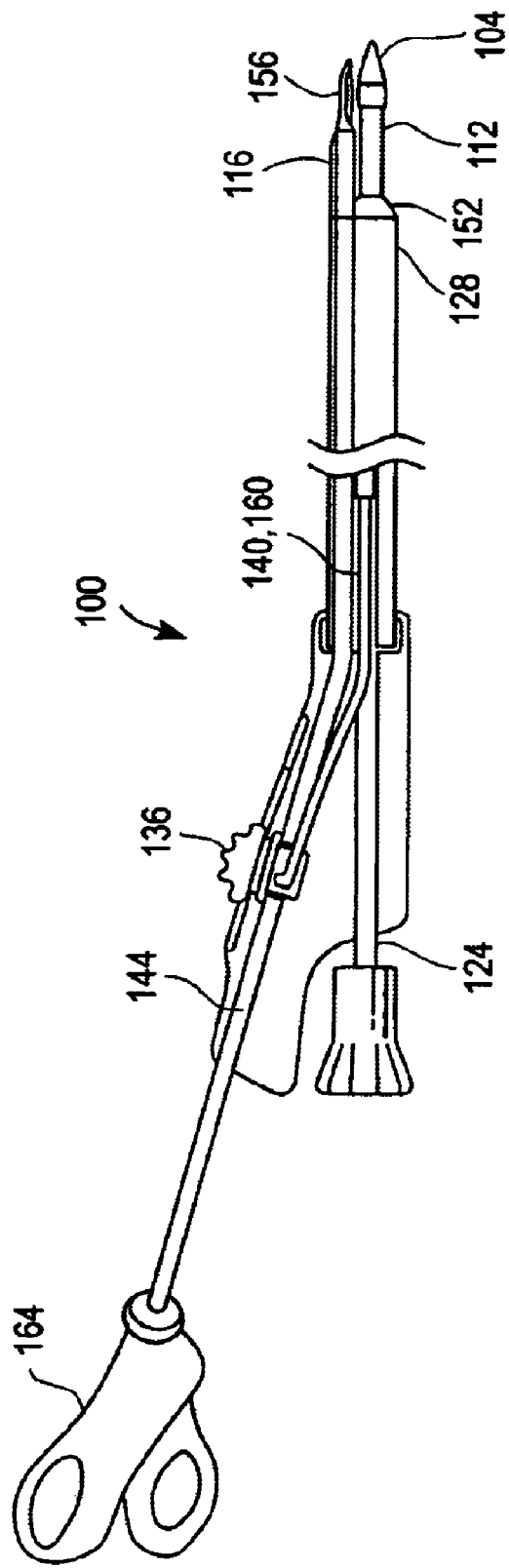
FIG. 1a is a perspective view diagram of an endoscopic cannula in accordance with the present invention.
Figure 1B:
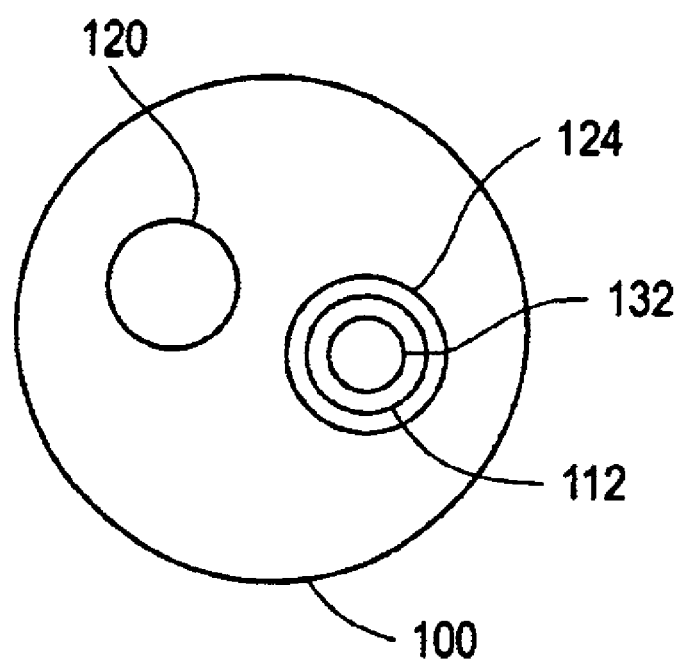

FIG. 1a illustrates an endoscopic cannula 100 in accordance with one embodiment of the present invention. The endoscopic cannula 100 preferably comprises an endoscopic lumen 124 for accommodating an endoscope 132 (not shown). FIG. 1b is a cut-away view of the endoscopic cannula 100 of FIG. 1a, and illustrates the endoscopic lumen 124 housing a conventional endoscope 132, typically of about 5 mm diameter, and a working lumen 120 for housing a surgical tool (not shown).

Referring back to FIG. 1a, the cannula 100 comprises an endoscopic dissection shaft 112 that extends out of a main body 128 of the cannula 100 for a length sufficient to allow the endoscopic dissection shaft 112 to be used for dissection and retraction without engaging tissue with the main body 128 of the cannula 100. In one embodiment, the endoscopic dissection shaft 112 extends beyond the main body 128 of the cannula 100 by approximately 4 cm. In one embodiment, the main body 128 of the endoscopic cannula 100 has a 12 mm diameter, although main bodies of other diameters typically depending upon the type and nature of the medical procedure to be performed with the cannula 100 may also be used in accordance with the present invention. The main body 128 diameter discussed herein is selected for an instrument in which a standard 5 mm endoscope will be used.

The endoscopic dissection shaft 112 has a distal end comprising a transparent tapered tip 104. Although a tapered transparent tip 104 is described herein, transparent tips having different or no tapered profiles may also be used in accordance with the present invention. The endoscopic dissection shaft 112 preferably has a shaft of decreased maximal dimension (diameter, if the endoscopic dissection shaft 112 is cylindrical) relative to the maximal dimension of the main body. In the embodiment described herein, the diameter of the endoscopic dissection shaft 112 is approximately 7 mm. Thus, the endoscopic dissection shaft 112 has a small cross-sectional profile to facilitate tissue dissection with low-level force applied, and to improve maneuverability of the tip within tissue being dissected. The main body 128 flares out to a larger cross-sectional profile to secondarily dilate tissue at a surgical site of interest.

In a preferred embodiment, the endoscopic lumen 124 extends through the endoscopic dissection shaft 112 to the transparent tapered tip 104. An endoscope 132 within the endoscopic lumen 124 provides endoscopic visualization through the transparent tapered tip 104 of tissue being dissected along the length of the vessel being harvested. In the preferred embodiment, the endoscope 132 is sealed within the endoscopic lumen 124 by the transparent tapered tip 104 to prevent smudging of the endoscope by surrounding blood or tissue. Since a working lumen 120 extends through the cannula and houses the surgical tools, the transparent tapered tip 104 which is positioned on the endoscopic dissection shaft 112 does not have to be removed from the cannula 100 to accommodate other endoscopic instruments during a surgical procedure. Thus, cautery scissors may be manipulated through the working lumen 120 to cauterize and transect tributaries of side branches of the vessel being harvested while the endoscope 132 remains enclosed within the transparent tapered tip during vessel harvesting, and thus remains unaffected by the presence of blood and tissue in the surgical field. Further, the transparent tip 104 may be placed against the main trunk of the vessel being harvested to displace the blood therein and promote visualization of the vessel in contrasting color. To further reduce the force required to advance the cannula 100 during blunt tissue dissection, the face 152 of the main body 128 at the point at which the endoscopic dissection shaft 112 extends is contoured, and such contoured face 152 allows tissue to slide easily past the cannula 100 with a minimum of force exerted against the tissue.

The working lumen 120 which extends through the main body 128 of the cannula between the proximal and distal ends thereof receives the surgical instruments therein that are required to perform surgical procedures. For example, surgical scissors may be housed in the working lumen 120 to transect and cauterize side branches during a procedure to harvest the saphenous vein. Alternatively, a bisector may be inserted into the working lumen 120 to perform such transection. As discussed above, the working lumen 120 ends proximal to the endoscopic lumen 124, allowing the smaller endoscopic dissection shaft 112 to provide a low profile for dissection and retraction. FIG. 1a illustrates an embodiment of the cannula 100 of the present invention in which flexible endoscopic scissors 156 are housed in the working lumen 120. In a preferred embodiment, a shaft 144 of the endoscopic scissors 156 is attached to an actuation device to manually control the length of extension of the scissors 156, or other tool. In the embodiment of FIG. 1a, the actuation device is a slidable button 136 attached to the scissor shaft 144 for extending or retracting the scissors 156, as needed. Alternatively, the scissors 156 can be manipulated by moving the handles 164 of the scissors 156 forward or backward with respect to the cannula 100.

In one embodiment, the scissors 156 are aligned to allow the concave curve of the blades of the scissors 156 to be disposed toward the transparent tapered tip. In this embodiment, the shaft 144 of the scissors 156 is keyed to the working lumen 120 to maintain the tips of the scissors 156 in a predetermined rotational orientation with respect to the transparent tapered tip 104. In a preferred embodiment, the shaft 144 is set to retain the blades of the scissors 156 curved inwardly toward the tip 104 of the device. This allows endoscopic visualization of the entire length of the scissors blades as a side branch is transected, thus facilitating a safe cutting process. FIG. 1a shows one technique for keying the scissors shaft 144 with respect to the transparent tapered tip 104. In the embodiment of FIG. 1a, the scissors shaft 144 is bonded to the slide button 136, preventing rotation of the scissors upon extension of the scissors. Additionally a wire 140 is attached to the button 136 that extends along a separate alignment lumen 160 in the cannula 100. The wire 140 from the slide button 136 translates axially along the alignment lumen 160 in the cannula 100, and also prevents the scissors shaft 148 from rotating. Fixing the rotational position of the scissors blades with respect to the transparent tapered tip 104 also simplifies side branch transection in an embodiment of the present invention adapted for harvesting a saphenous vein, as the only degree of rotation possible involves rotation of the cannula 100 with respect to the side branch. Thus, the surgeon can easily position a side branch to be within the predetermined extension position of the endoscopic shears 156. Thus, this embodiment of the cannula 100 decreases the time required to perform a saphenous vein harvesting procedure. In contrast, conventional systems required rotation of the cannula as well as rotation of the scissors at each side branch creating a more complicated process than the process of the present invention.

In one embodiment, a flexible, preferably elastic, hood 116 extends from the distal end of the working lumen 120 to the proximal edge of the transparent tapered tip 104. The hood 116 expands or otherwise displaces to allow a surgical tool to be extended from the working lumen 120, and collapses against the surface of the cannula 100 upon retraction of the surgical tool. Thus, the flexible hood 116 provides a tapered profile for the cannula 100 from the endoscopic dissection shaft 112 to the larger diameter main body 128 of the cannula 100. The flexible hood 116 is preferably constructed of a smooth and elastic bio inert material such as latex or silicone rubber or polyurethane or polyethylene to render the surface of the cannula 100 slippery upon contact with subcutaneous tissue. This further reduces the force required to dissect tissue during cannula advancement. Edges of the hood 116 are attached to the surface of the cannula 100 to provide a resistive force as the surgical tool is extended there through. The distal end of the hood 116 is preferably tapered, to further minimize the force exerted by the hood 116 on surrounding tissue. In an embodiment in which surgical scissors 156 are used for saphenous vein harvesting, the flexible hood 116 covers the scissors blades as the scissors 156 are being advanced out of the second lumen to prevent the scissors 156 from catching vessel branches or connective tissue along sides of the surgical site.

FIGS. 2a and 2b illustrate advancement of a surgical tool through the flexible hood 116. In FIG. 2a, the surgical tool is shown as being retracted into the cannula 100, and thus the flexible hood 116 tapers along the endoscopic dissection shaft 112 to the distal face 152 of the main body 128. This provides a smooth sliding surface for tissue dissection. In FIG. 2b, a surgical tool such as endoscopic scissors 156 are extended through the flexible hood 116. The hood 116 is flexible and expands to accommodate extension and exposure of the scissors 156 for use during transection and cauterization, as required.

Figure 4:
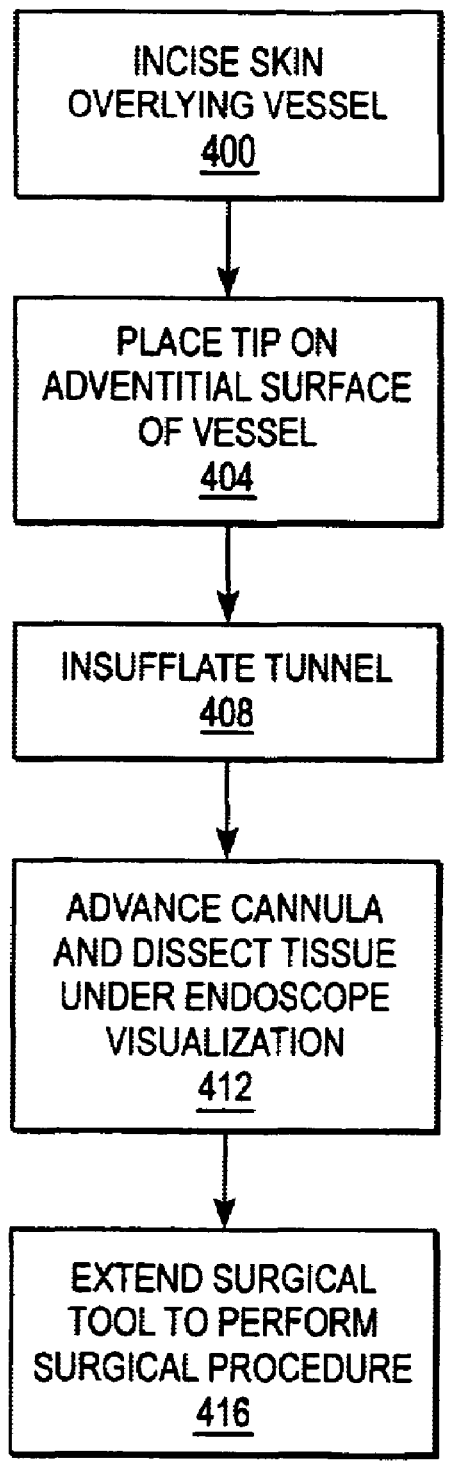
FIG. 4 is a flowchart illustrating a method of using the endoscopic cannula of the present invention.

FIGS. 3a and 3b illustrates a use of the cannula 100 to transect a tributary or side branch 308 of a vein 300. FIG. 4 is a flow chart illustrating a method of using the cannula 100, and will be described in conjunction with FIGS. 3a and 3b. Initially, a conventional sliding gas-sealing port such as the Blunt Tip Trocar (BTT, Guidant Corporation, Cardiac and Vascular Surgery, Menlo Park, Calif.) is backloaded onto the cannula 100. Then, the skin overlying the vessel 300 is incised 400 with approximately an 1.5–2 cm incision. The vessel 300 is isolated, and the transparent tapered tip 104 is placed 404 on the adventitial surface of the vessel 300 and advanced along the vessel 300 a sufficient length to allow insertion of the port into the incision. The port seals the incision and gas insufflation is initiated 408 to create a working tunnel or anatomical space adjacent the vessel being harvested. Under insufflation and endoscopic visualization, the cannula 100 is advanced 412 along the vessel 300. The transparent tapered tip 104 provides initial blunt tissue dissection and the main body 128 of the cannula 100 provides secondary tissue dilation. The tapered flexible hood 116 is collapsed along the side of the endoscopic dissection shaft 112 to provide a low profile for the cannula 100 as it is maneuvered within the surgical site. A surgical tool 156 such as bipolar scissors may be extended 416 from the cannula 100 through the flexible hood 156 to perform an ancillary surgical procedure. For saphenous vein harvesting procedures, the cannula 100 is advanced arteriorly and posteriorly along the length of the vessel 300, and on either side of each tributary or side branch. Upon encountering a side branch 308, as shown in FIG. 3a, the transparent tapered tip 104 is advanced to the apex 304 between the main trunk of the vein 300 and the side branch 308. The center of the tapered tip 104 is placed against the main trunk of the vessel. As shown in FIG. 3b the scissors 156 are advanced 416, and the cannula 100 is rotated if necessary to direct the scissors blades toward the side branch 308 for cauterization and transection. Alternatively, a bisector of hook-like configuration may be used. In this embodiment, the hook-like bisector is positioned in the working lumen 120 and can be extended from the cannula 100 to loop around the side branch 308 to transect and cauterize the side branch 308 upon retraction into the lumen 120.

Figure 5:
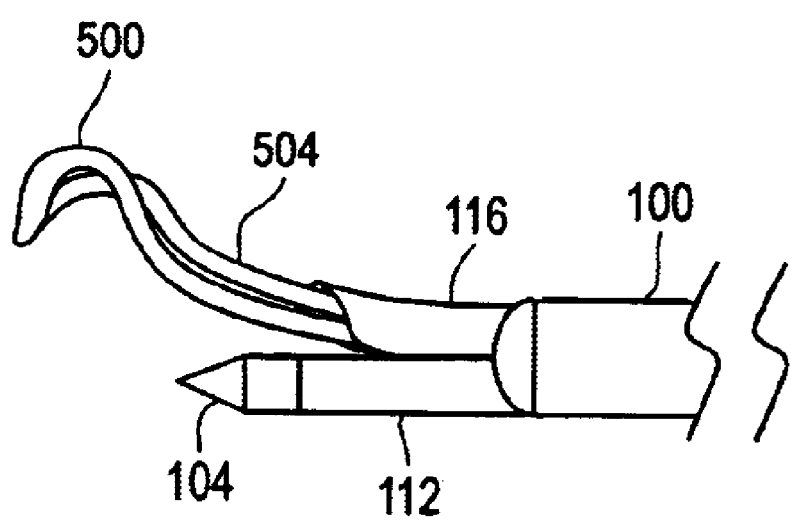
FIG. 5 is a perspective view of an embodiment of the endoscopic cannula comprising a retractor according to the present invention.

In another embodiment, as shown in FIG. 5, a cradled retractor 504 configured with a hook-like, U-shaped cradle 500, is positioned within the working lumen 120. The cradled retractor 504 is preferably a retractor such as described in U.S. Pat. No. 5,895,353. However, other cradled retractors sized to fit within the working lumen 120 could also be used in accordance with the present invention. In this embodiment, after the side branches have been transected and cauterized, the bipolar scissors or bisector or other surgical site and the surgical tool is removed from the working lumen 120. Then, the cradled retractor 504 is placed within the lumen 120 and is extended from the distal end thereof from beneath the hood 116 with the cradle 500 placed over the proximal end of the vein to be harvested. The cradle 500 is then passed along the length of the vein to ensure that all of the side branches have been transected. If a side branch is encountered, bipolar scissors or bisector is reinserted into the lumen 120 in the cannula 100, and is extended to transect the side branch. Replacement of surgical tools within the working lumen 120 may be accomplished with the cannula 100 in position within the surgical site, or with the cannula removed from the surgical site through the gas-sealing port.

Figure 6A:
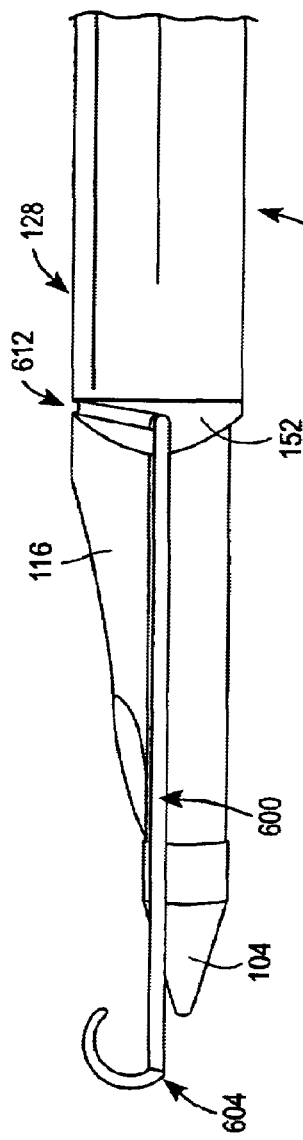
FIGS. 6a–c are perspective views of an embodiment of the endoscopic cannula comprising a dissection loop according to the present invention.
Figure 6B:
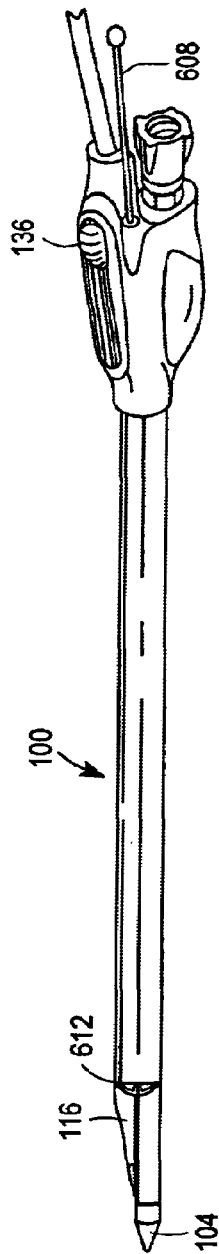
Figure 6C:
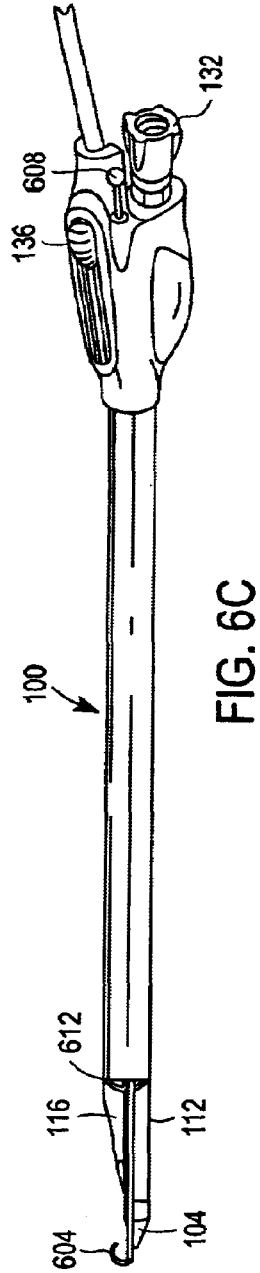

FIG. 6a illustrates an alternate embodiment in which a dissection loop instrument 600 is incorporated into the cannula 100. In this embodiment, third and fourth lumens are disposed in the cannula 100 to house the dissection loop instrument 600. The dissection loop 604 is a curved metal or plastic piece attached to the distal end of the dissection loop instrument 600. The dissection loop 604 is preferably an open loop of about 180° arc that is contiguous with two shafts running axially the length of the cannula. The shafts are generally made of stainless steel, and they may be solid or tubular. Alternatively, the dissection loop 604 and the shafts may be formed of a single piece of stainless steel wire. A storage groove 612 is sized to accommodate the dissection loop 604 and is disposed on the distal end of the main body 108 of the cannula 100. The dissection loop 604 can be docked into the storage groove 612 when not in use. In use, following transection of all tributaries arising from the vessel, the dissection loop 604 may be passed along the length of the vessel to ensure that all tributaries or side branches have been severed, and can provide additional tissue dissection or vessel retraction as required. By passage of the loop axially along the vessel, adherent strands of connective tissue are dissected away from the vessel. FIG. 6*b* illustrates one stem 608 at the dissection loop extending proximally out of the cannula 100 from the third lumen. As shown in FIG. 6*c*, the dissection loop stem 608 may be manually moved forward axially to displace the dissection loop 604 out of the storage groove 612 and extend it beyond the distal end of the transparent tapered tip 104, thus allowing the loop 604 to be positioned adjacent the vessel of interest.

What is claimed is:

1. Surgical apparatus comprising an elongated cannula further comprising:
   a first lumen extending within the cannula between proximal and distal ends thereof for housing an endoscope therein;
   a transparent tip disposed at the distal end of the first lumen for performing tissue dissection and providing endoscopic visualization therethrough;
   a second lumen eccentric the first lumen and having an open distal end positioned proximal to the distal end of the first lumen for housing a medical instrument therein to protrude from the open distal end for performing procedures on tissue viewed through the transparent tip; and
   a flexible hood extending from the distal end of the second lumen and gradually tapering down towards the distal end of the first lumen, the hood maintaining its tapered configuration even in the absence of a medical instrument in the second lumen, to form a smooth transition surface adjacent the transparent tip to facilitate blunt tissue dissection and maneuverability, wherein the flexible hood comprises an open distal end and wherein the flexible hood assumes expanded configuration in response to extension through the distal end thereof of the medical instrument projecting from the open distal end of the second lumen and through the open distal end of the hood.

2. The apparatus of claim 1 further comprising at least one additional lumen.

3. The apparatus of claim 1 wherein the second lumen houses scissors.

4. The apparatus of claim 3 wherein a rotational orientation of the scissors is fixed relative to the transparent tip.

5. The apparatus of claim 1 wherein the second lumen houses a dissection loop.

6. The apparatus of claim 1 wherein the second lumen houses a retractor for cradling a vein.

7. The apparatus of claim 1 wherein the second lumen houses a tool for use in vessel harvesting procedure.

8. The apparatus of claim 1 wherein the hood is constructed of a material selected from the group consisting of latex, silicone rubber, polyurethane and polyethylene.

9. The apparatus of claim 1 wherein a distal end of the hood extends substantially to a proximal edge of the transparent tip.

10. The apparatus of claim 1 wherein the transparent tip is not removable.

* * * * *